United States Patent [19]

Falcone et al.

[11] 4,381,403

[45] Apr. 26, 1983

[54] PROCESS FOR THE PREPARATION OF N-MONOSUBSTITUTED CARBAMIC ACID ESTERS

[75] Inventors: Samuel J. Falcone, West Chester; John J. McCoy, Media, both of Pa.

[73] Assignee: Atlantic Richfield Company, Los Angeles, Calif.

[21] Appl. No.: 135,946

[22] Filed: Mar. 31, 1980

[51] Int. Cl.$^3$ ............... C07C 125/065; C07C 125/073
[52] U.S. Cl. ......................................... 560/24; 560/9; 560/10; 560/12; 560/13; 560/25; 560/27; 560/28; 560/29; 560/33
[58] Field of Search .................. 560/24, 25, 9, 10, 12, 560/13, 27, 28, 29, 33

[56] References Cited

U.S. PATENT DOCUMENTS 2,409,712 10/1946 Schweitzer ........................... 560/24
2,806,051 9/1957 Brockway ............................. 560/24
2,943,108 6/1960 Newcomer et al. .................. 560/24

*Primary Examiner*—Bernard Helfin
*Attorney, Agent, or Firm*—Delbert E. McCaslin

[57] ABSTRACT

A process for the preparation of N-monosubstituted carbamic acid esters by reacting an unsubstituted carbamic acid ester and an aromatic primary amine at a suitable pressure and reaction temperature in the presence of a monohydric aliphatic alcohol and preferably in the presence of a strongly basic tertiary amine as catalyst. Optionally an inert co-solvent in addition to the alcohol may be employed.

21 Claims, No Drawings

PROCESS FOR THE PREPARATION OF N-MONOSUBSTITUTED CARBAMIC ACID ESTERS

BACKGROUND OF THE INVENTION

U.S. Pat. No. 3,161,676 describes a process for the preparation of a substituted alkyl urea by reacting a carbamic acid ester with a primary and sterically unhindered secondary aliphatic amines in the presence of a metal compound Lewis acid catalyst, such as cupric acetate.

There is no known prior art which describes the preparation of N-monosubstituted carbamic acid esters by reacting an unsubstituted carbamic acid ester and an aromatic primary amine in the presence of a monohydric aliphatic alcohol with or without the use of a tertiary amine catalyst.

Many important commercial applications have been developed for the carbamic acid ester products of this invention, for example, as agricultural chemicals and chemical intermediates which may be converted to the corresponding isocyanate and alcohol by thermal decomposition or other methods described in the prior art.

SUMMARY OF THE INVENTION

The present invention is based on the unexpected discovery that it is possible to produce, in high yield and high conversions of reactants, an N-substituted carbamate, such as ethylphenylcarbamate (ethyl N-phenylcarbamate), by the reaction of an aromatic primary amine such as aniline with an unsubstituted carbamate such as ethyl carbamate at a temperature of from about 125° C. to 250° C. in the presence of a monohydric aliphatic alcohol and preferably in the presence of a tertiary amine catalyst. While the alcohol employed may, among other things, function as a solvent to effect the reaction, a co-solvent in addition to the alcohol may alternatively be used in the process of the invention.

It is a primary object of this invention therefore, to provide a novel process for the preparation of N-monosubstituted carbamates.

It is another object of this invention to provide a novel reaction system for the conversion of an unsubstituted carbamic acid ester and an aromatic primary amine to N-monosubstituted carbamic acid esters, such as ethylphenylcarbamate.

These and other objects and advantages of this invention will become apparent from the description of the invention which follows, and from the claims.

DETAILED DESCRIPTION OF THE INVENTION

In accordance with this invention an N-substituted carbamic acid ester is produced by reacting an unsubstituted carbamic acid ester of the general formula $NH_2CO_2R$ wherein R is a straight or branched chain alkyl group containing from 1 to 10 carbon atoms, with a primary aromatic amine of the general formula $R'(NH_2)n$ wherein R' may be a substituted or unsubstituted aryl or aralkyl group containing one or more benzenoid rings, preferably not more than six, which may be fused or joined by single valency bonds, directly or through bridging groups which may be, for example, oxygen or sulfur or a methylene group at a temperature in the range of from about 125° C. to 250° C. in the presence of a monohydric aliphatic alcohol having from 1 to 10 carbon atoms and preferably in the presence of a tertiary amine catalyst. Alternatively an inert solvent in addition to the alcohol may be employed. The R and R' may also contain substituents which do not interfere with the reaction, such as alkoxy, sulfur, sulfoxide, sulfone, etc. radicals. n is an integer of 1 to 6.

The reaction between the unsubstituted carbamic acid ester and the aromatic primary amine may be carried out in any suitable reactor, such as an autoclave, which is generally equipped with a means for agitation, means for regulating temperature and pressure and means for removing by-product ammonia, and possibly alcohol vapor. Although the order of addition of the reactants, alcohol and solvents and catalyst components, if any, may vary, a general procedure for carrying out the reaction is to charge the unsubstituted carbamic acid ester, primary aromatic amine, alcohol and, preferably, a strongly basic tertiary amine catalyst into the reaction vessel and then heat the mixture to the desired temperature at atmospheric pressure or higher pressures, if required. The reaction can be carried out batchwise, semicontinuous, or as a continuous process. The reaction products are recovered and treated by any conventional method, such as distillation or fractionation to effect separation of the N-monosubstituted carbamate from unreacted starting material, catalyst, solvent and by-products.

The unsubstituted carbamic acid esters employed as reactants in the process of the present invention conform to the general formula $NH_2CO_2R$ wherein R is a substituted or unsubstituted straight or branched chain alkyl group containing from 1 to 10 carbon atoms. Representative unsubstituted carbamic acid esters suitable for use in this invention include, for example, methyl carbamate, ethyl carbamate, normal and isobutylcarbamates, propyl carbamate, amyl carbamate, isoamyl carbamate, hexyl carbamate, octyl carbamate, 2-ethylhexyl carbamate, decyl carbamates, heptyl carbamate, nonyl carbamate, 2 ethyl-1-butyl carbamate, 3,5-dimethyl-1-hexyl carbamate, and the like. In general, the methyl and ethyl esters and more readily available and are, therefore, more preferred.

The aromatic primary amines employed as reactants in the process of the present invention conform to the general formula $R'(NH_2)n$ wherein R' is a substituted or unsubstituted aryl or aralkyl group containing one or more benzenoid rings, preferably not more than six, which may be fused or joined by single valency bonds directly or through bridging groups which may be, for example, oxygen or sulfur or a methylene group; n is 1 to 6. Representative amines as hereinabove described include, for example, aniline, toluidines, naphthylamines, benzylamines, xylidines, xylene diamines, naphthalene diamines, toluene diamines, xylylene diamines, anisidines, phenetidines, 3,3'-dimethyl-4,4'-diphenyldiamine, phenylenediamines, 2,4'- and 4,4'-methylenedianiline, sulfonyldianilines, dimethylbenzylamine, naphthalenemethylamines, dimethyl and diethylbenzidines, methyl and ethylthioanilines, biphenylamines and diamines, phenoxyanilines, thiodianilines, and the like. The polyamine made by condensing aniline with formaldehyde and used, for example, in the preparation of polymeric isocyanates may also be employed. In general, aniline and the toluene diamines are preferred.

The alcohols which are employed are monohydric aliphatic alcohols containing from 1 to 10 carbon atoms. It is generally preferred that the alcohol employed correspond to the alkyl group of the reactant unsubstituted carbamic acid ester in order to prevent the preparation of mixed N-substituted carbamates. The alcohols, in addition to acting as the reaction solvent, substantially inhibit side reactions and are generally employed in a molar excess based on the amine or unsubstituted carbamic acid ester reactants, i.e., from about a molar ratio of 0.5:1 to 15:1 of alcohol to amine or carbamate reactant employed to produce the N-substituted carbamic acid esters. Representative alcohols which may be employed in the process of this invention include, for example, methanol, ethanol, n-propanol, n- and iso-butyl alcohols, amyl alcohol, hexanol, heptanol, octanol, nonanol, decanol, 2-ethyl hexanol, 2-methyl pentanol, 2-ethyl-1-butanol, 3,5-dimethyl-1-hexanol, and the like. The lower aliphatic alcohols having 1 to 4 carbon atoms are preferred.

A general postulated equation for the reaction of the present invention may be represented as follows:

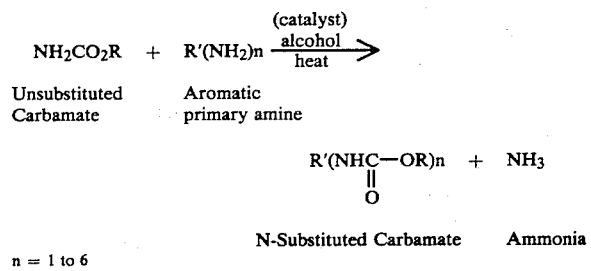

n = 1 to 6 wherein R and R' are as hereinabove described. A wide variety of N-substituted carbamates can be prepared by the process of this invention.

Although an optional feature of this invention, it has also been discovered that improved yields and increased reaction rates can be obtained when the above reaction is carried out in the presence of a strongly basic tertiary amine catalyst. The tertiary amine catalysts may be an aliphatic, cycloaliphatic, araliphatic or aromatic amine containing from 1 to 18 carbon atoms, which may be interrupted by oxygen, sulfur, nitrogen, sulfoxide or carbonyl substituents. In general, the amine employed as catalyst should be easily separated from reaction product and by-products. Representative amines suitable for use in the process of the invention include, for example, the trialkylamines such as the trimethyl, triethyl, tripropyl, tributyl, trihexyl, trioctyl, tridecyl, tridodecyl, etc. amines, triphenylamine, n-dodecyldimethylamine, n-tetradecyldimethylamine, n-hexyldecyldimethylamine, n-octyldecyldimethylamine, N,N,N',N'-tetramethylethylenediamine, N,N-dioctyl-1-octylamine, 1,4-diazabicyclo[2.2.2]octane, 4(N,N-dimethylamino) pyridine, pyridine, 1,5-diazabicyclo[3.4.0]non-5-ene, 1,8-diazabicyclo[5.4.0]-undec-7-ene, 1,1,3,3-tetramethylbutylamine, methyldiethylamine, butyldimethylamine, benzyldimethylamine, and the like. The amount of tertiary amine catalyst which can be used in the process will generally range between about 0.01 to 30 mole percent, preferably 0.1 to 20 mole percent based on the aromatic primary amine employed in the reaction, but greater or lesser quantities may be used if desired.

Although the process of the invention is preferably carried out using the monohydric aliphatic alcohol as the reaction solvent, other solvents or mixtures of solvents which are stable and substantially chemically inert to the components of the reaction system may be employed as a co-solvent in the reaction system if desired. Suitable co-solvents which may be employed, and generally in amounts of from 0 to 50 weight percent based on the reaction mixture, include, for example, benzene, toluenes, xylenes, dichlorobenzene, tetrahydrofuran, 1,2-dimethoxyethane, diphenylether, nitrobenzene, diethyleneglycol dimethyl ether, triethyleneglycol dimethyl ether, dimethylsulfoxide, and the like.

The ratio of reactants, i.e., unsubstituted carbamic acid ester and aromatic primary amine may be varied over any convenient range. The mole ratio of amine to unsubstituted carbamate may be between about 10:1 to 0.1:1 and is preferably between about 5:1 to 0.25:1.

The reaction of the present invention will proceed at temperatures of from about 125° C. to 250° C. It is generally preferred to operate the process at temperatures of from about 175° C. to 225° C. to obtain a convenient rate of reaction. The reaction temperature will depend on the particular N-substituted carbamic acid ester being produced and should be below the temperature at which significant decomposition of the product ester might occur.

The process of the present invention is generally carried out at atmospheric pressure, although higher pressures of up to 50 atmospheres may be used and especially at the higher reaction temperatures or when the reaction temperature is above the boiling point of the alcohol and/or reactant amine. Subatmospheric pressures may be employed, if desired.

Ammonia resulting from the reaction must be removed during the course of the reaction, otherwise reduced yields of product carbamate are obtained. When the reaction is carried out at one atmosphere the ammonia is simply allowed to escape from the reaction vessel. In reactions where elevated pressures are employed provisions must be made to remove ammonia. A simple, convenient method is to strip the ammonia from the reactor with a dry inert gas, such as nitrogen or carbon dioxide and/or with the resulting alcohol vapor provided the alcohol employed is volatile at the reaction temperature. When the alcohol vapor is used to strip or aid in stripping the ammonia from the reactor, additional or makeup alcohol can be added to the reactor at a rate to compensate for the vapor loss.

The reaction time is generally dependent on the N-monosubstituted carbamate being produced, the reaction temperature and the catalyst employed, if any, and will vary depending on whether the process if continuous or batch but will generally range between about one to several hours.

The following Examples are provided to illustrate the invention in accordance with the principles of this invention, but are not to be construed as limiting the invention in any way except as indicated by the appended claims.

In the Examples which follow, the reactions were run in a 300 ml stainless steel stirred autoclave. The amine, unsubstituted carbamic acid ester and alcohol, along with tertiary amine catalyst and co-solvent, if any, are charged to the reactor which is then flushed with nitrogen and the reactor heated to the desired reaction temperature for a specified time period. During the reaction vaporized alcohol and product ammonia are stripped from the reactor with or without the aid of an inert gas. Makeup alcohol is pumped into the reactor at a rate closely approximating the alcohol removed. At the end of the reaction time, the autoclave is cooled to ambient temperature and the contents combined with the stripped alcohol which was collected in a dry ice cooled trap and the total mixture analyzed by liquid chromatography (LC) for conversion of amine and unsubstituted carbamic acid ester and selectivities to N-monosubstituted carbamate. Amine and the unsubstituted carbamate conversions were calculated on the basis of moles of the amine and carbamate consumed by the reaction. Product selectivities were based on the moles of amine or unsubstituted carbamate consumed in preparing the N-monosubstituted carbamate and by-products.

EXAMPLE 1

23.3 g aniline, 22.2 g ethyl carbamate and 220 ml of dry ethanol (200 proof) was charged to the autoclave which was flushed several times with nitrogen and heated to 200° C. for a period of 3 hours. During the reaction period ethanol and ammonia were stripped from the reactor with nitrogen at an average of 1.7 ml of ethanol per minute. The ethanol vapor containing ammonia and a small amount of aniline was condensed in a dry ice cooled trap. Makeup ethanol was pumped into the autoclave at a rate closely approximating the amount stripped. After the reaction period, the autoclave was cooled and the contents along with the ethanol condensate analyzed. LC analysis showed an aniline conversion of 34 percent and an ethylcarbamate conversion of 47.2 percent with selectivities to ethylphenylcarbamate of 79 mole percent and 47.2 mole percent based on aniline and ethylcarbamate, respectively.

EXAMPLE 2

Example 1 was repeated using 100 ml ethanol and 100 ml benzene co-solvent. Analysis of the product and ethanol condensate showed an aniline conversion of 54 percent and an ethylcarbamate conversion of 65 percent. Selectivities to ethylphenylcarbamate was 75 mole percent and 62 mole percent based on aniline and ethylcarbamate, respectively.

EXAMPLE 3

Example 1 was repeated using 0.76 g 1,8-diazabicyclo[5.4.0]undec-7-ene as catalyst. Analysis showed an aniline conversion of 62.4 percent and an ethylcarbamate conversion of 84 percent with selectivities to ethylphenylcarbamate of 96.5 mole percent and 71 percent based on aniline and ethylcarbamate, respectively.

EXAMPLE 4

Example 2 was repeated using 100 ml diphenylether as a co-solvent, along with 0.4 mole of pyridine as catalyst. Analysis showed an aniline conversion of 55 percent and an ethylcarbamate of 66 percent with selectivities to ethylphenylcarbamate based on aniline and ethylcarbamate of 92 and 86 mole percent, respectively.

EXAMPLES 5 TO 23

In Examples 5 to 23, which follow in Table form, the general procedure as hereinabove described was repeated using various amines, unsubstituted carbamic acid esters, alcohols, tertiary amine catalysts and conditions as shown in Table 1. The results are set forth in Table 2.

TABLE 1

| Example No. | Amine | Unsubstituted Carbamate (Moles) | | Alcohol | | Catalyst | | Temperature | Time |
|---|---|---|---|---|---|---|---|---|---|
| 5. | Aniline | .25 | Ethyl carbamate | .25 | Ethanol 3.8 | — | | 150° C. | 4 hrs |
| 6. | Aniline | .25 | Ethyl carbamate | .25 | Ethanol 3.8 | — | | 200° C. | 3 hrs |
| 7. | Aniline | .25 | Ethyl carbamate | .25 | Ethanol 3.8 | DBU[1] | .006 | 200° C. | 3 hrs |
| 8. | Aniline | .25 | Ethyl carbamate | .25 | Ethanol 1.7 | DBU | .006 | 200° C. | 3 hrs |
| 9. | Aniline | .75 | Ethyl carbamate | .05 | Ethanol 2.2 | DBU | .005 | 200° C. | 3 hrs |
| 10. | Aniline | .75 | Ethyl carbamate | .05 | Ethanol 1.1 | DBN[2] Pyridine | .005 .83 | 200° C. | 2 hrs |
| 11. | Aniline | .64 | Ethyl carbamate | .64 | Ethanol 1.8 | DBN | .006 | 200° C. | 3 hrs |
| 12. | Aniline | .54 | Ethyl carbamate | .54 | Ethanol 2.2 | TOA[3] | .005 | 200° C. | 3 hrs |
| 13. | Aniline | .64 | Ethyl carbamate | .64 | Ethanol 2.7 | TOA | .06 | 200° C. | 2 hrs |
| 14. | Aniline | .64 | Ethyl carbamate | .64 | Ethanol 2.4 | Pyridine | .4 | 200° C. | 3 hrs |
| 15. | Aniline | .64 | Ethyl carbamate | .64 | Ethanol 0.85 | TEA[4] | .68 | 200° C. | 3 hrs |
| 16. | Aniline | .64 | Ethyl carbamate | .64 | Ethanol 2.7 | TPA[5] | .003 | 200° C. | 2 hrs |
| 17. | Aniline | .64 | Ethyl carbamate | .64 | Ethanol 2.7 | TPA | .06 | 200° C. | 3 hrs |
| 18. | Aniline | .64 | Methyl carbamate | .64 | Methanol 3.2 | TEA | .1 | 200° C. | 3 hrs |
| 19. | β-Naphthylamine | .64 | Methyl carbamate | .64 | Methanol 3.5 | DBU | .006 | 200° C. | 3 hrs |
| 20. | 2,4-Toluene-Diamine | .32 | Ethyl carbamate | .64 | Ethanol 3.0 | DBN | .005 | 200° C. | 3 hrs |
| 21. | Aniline | .64 | Octyl carbamate | .64 | Octanol 2.7 | TEA | .5 | 200° C. | 3 hrs |
| 22. | Aniline | .64 | Ethyl carbamate | .64 | Ethanol 3.0 | TEA | .3 | 175° C. | 3 hrs |
| 23. | Aniline | .64 | Ethyl carbamate | .64 | Decanol 3.0 | TEA | .68 | 210° C. | 2 hrs |

[1] DBU 1,8-Diazabicyclo[5.4.0]undec-7-ene
[2] DBN 1,5-Diazabicyclo[4.3.0]non-5-ene
[3] TOA Tri-n-octylamine
[4] TEA Triethylamine
[5] TPA Tri-n-propylamine

TABLE 2

| Example No. | Amine Mole Percent Conversion | Amine Mole Percent N—mono-substituted Carbamate Selectivity | Unsubstituted Carbamate Mole Percent Conversion | Unsubstituted Carbamate Mole Percent N—mono-substituted Carbamate Selectivity |
|---|---|---|---|---|
| 5. | 30 | EPC[6] 60 | 29 | EPC[6] 65 |
| 6. | 34 | EPC 79 | 47 | EPC 58 |
| 7. | 46 | EPC 86 | 59 | EPC 67 |
| 8. | 61 | EPC 97 | 85 | EPC 71 |
| 9. | 55 | EPC 87 | 82 | EPC 88 |
| 10. | 61 | EPC 73 | 95 | EPC 70 |
| 11. | 67 | EPC 95 | 69 | EPC 93 |
| 12. | 54 | EPC 92 | 49 | EPC 100 |
| 13. | 57 | EPC 82 | 61 | EPC 78 |
| 14. | 55 | EPC 92 | 59 | EPC 85 |
| 15. | 86 | EPC 92 | 89 | EPC 90 |
| 16. | 21 | EPC 97 | 20 | EPC 98 |

TABLE 2-continued

| Example No. | Amine | | Unsubstituted Carbamate | |
|---|---|---|---|---|
| | Mole Percent Conversion | Mole Percent N—mono-substituted Carbamate Selectivity | Mole Percent Conversion | Mole Percent N—mono-substituted Carbamate Selectivity |
| 17. | 38 | EPC[6] 78 | 43 | EPC[6] 66 |
| 18. | 62 | MPC[7] 85 | 64 | MPC[7] 83 |
| 19. | 50 | MNC[8] 87 | 55 | MNC[8] 79 |
| 20. | 85 | DETC[9] 90 | 45 | DETC[9] 85 |
| 21. | 56 | OPC[10] 80 | 58 | OPC[10] 77 |
| 22. | 24 | EPC 96 | 29 | EPC 91 |
| 23. | 48 | EPC 85 | 57 | EPC 68 |

[6]EPC Ethylphenyl carbamate
[7]MPC Methylphenyl carbamate
[8]MNC Methylnaphthyl carbamate
[9]DETC 2,4-diethyltolyldicarbamate
[10]OPC octylphenyl carbamate

We claim:

1. A process for the preparation of an N-monosubstituted carbamic acid ester which comprises reacting an unsubstituted carbamic acid ester having the formula $NH_2CO_2R$ wherein R is a straight or branched chain alkyl group containing from 1 to 10 carbon atoms, with an aromatic primary amine having the formula $R'(NH_2)n$ wherein R' is a substituted or unsubstituted aryl or aralkyl group containing one or more benzenoid rings which may be fused or joined by single valency bonds and n is an integer of 1 to 6, at a temperature in the range of from about 125° C. to 250° C. in the presence of a monohydric aliphatic alcohol having from 1 to 10 carbon atoms and a catalytic amount of from about 0.01 to 30 mole percent based on the aromatic primary amine employed of a tertiary amine which may be an aliphatic, cycloaliphatic, aryliphatic or aromatic amine containing from 1 to 18 carbon atoms.

2. A process according to claim 1 wherein the unsubstituted carbamic acid ester is selected from the group consisting of methylcarbamate, ethylcarbamate, and octylcarbamate.

3. A process according to claim 2 wherein the unsubstituted carbamic acid ester is ethyl carbamate.

4. A process according to claim 1 wherein the aromatic primary amine is selected from the group consisting of aniline, toluene diamines and naphthylamines.

5. A process according to claim 4 wherein the aromatic primary amine is aniline.

6. A process according to claim 1 wherein the reactant aromatic primary amine to unsubstituted carbamic acid ester is employed at a molar ratio of from about 10:1 to 0.1:1.

7. A process according to claim 6 wherein the molar ratio employed is from about 5:1 to 0.25:1.

8. A process according to claim 1 wherein the alcohol is employed at a molar ratio of from about 0.5:1 to 15:1 based on the amine or unsubstituted carbamic acid reactant.

9. A process according to claim 1 wherein the monohydric aliphatic alcohol is selected from the group consisting of methanol, ethanol, octanol and decanol.

10. A process according to claim 9 wherein the alcohol is ethanol.

11. A process according to claim 9 wherein the alcohol is methanol.

12. A process according to claim 1 wherein the tertiary amine is employed in a catalytic amount of from 0.1 to 20 mole percent of the aromatic primary amine employed.

13. A process according to claim 1 wherein the tertiary amine is selected from the group consisting of triethylamine, tri-n-propylamine, tri-n-octylamine, pyridine, 1,5-diazabicyclo[4.3.0]non-5-ene and 1,8-diazabicyclo[5.4.0]undec-7-ene.

14. A process according to claim 13 wherein the tertiary amine is triethylamine.

15. A process according to claim 13 wherein the tertiary amine is pyridine.

16. A process according to claim 13 wherein the tertiary amine is 1,8-diazabicyclo[5.4.0]undec-7-ene.

17. A process according to claim 1 wherein the reaction temperature is in the range of from about 175° C. to 225° C.

18. A process according to claim 1 wherein the reaction is carried out under a pressure of from 1 to 50 atmospheres.

19. A process according to claim 1 wherein the reaction is carried out in the presence of an inert solvent in addition to the alcohol.

20. A process for the preparation of ethylphenylcarbamate which comprises reacting ethylcarbamate with aniline at a temperature of from about 175° C. to 225° C. at a molar ratio of aniline to ethylcarbamate in the range of from 5:1 to 0.25:1 in the presence of ethyl alcohol and a catalytic amount of from 0.1 to 20 mole percent triethylamine.

21. A process according to claim 20 wherein the reaction is carried out in the presence of an inert solvent.

* * * * *